United States Patent [19]

Prisbylla

[11] 4,421,547

[45] Dec. 20, 1983

[54] 4-HYDROXY-5-ISOPROPYL-2-METHYL-PHENYL TRIMETHYLAMMONIUM, 1-PIPERIDINE CARBOXYLATE SALT OF N-PHOSPHONOMETHYLGLYCINE AND ITS USE AS A HERBICIDE

[75] Inventor: Michael P. Prisbylla, Richmond, Calif.

[73] Assignee: Stauffer Chemical Company, Westport, Conn.

[21] Appl. No.: 364,397

[22] Filed: Apr. 6, 1982

[51] Int. Cl.³ .............. C07D 295/18; C07F 9/65; C07F 9/38; A01N 57/20; A01N 57/24; A01N 37/46
[52] U.S. Cl. .......................................... 71/86; 546/226
[58] Field of Search ........................... 71/86; 546/226

[56] References Cited

U.S. PATENT DOCUMENTS

| | | | |
|---|---|---|---|
| 3,230,069 | 1/1966 | Preston | 546/226 |
| 3,506,434 | 4/1970 | Jacobi et al. | 71/89 |
| 3,799,758 | 3/1974 | Franz | 71/86 |
| 3,867,127 | 2/1975 | Fischer | 71/86 |
| 3,977,860 | 8/1976 | Franz | 71/86 |
| 4,071,551 | 1/1978 | Jung et al. | 71/86 |

OTHER PUBLICATIONS

Wirwille, J. W. et al., Chemical Abstracts (1950) 44:7447d.
Marth, P. C. et al., Chemical Abstracts 48:9605i.

*Primary Examiner*—Norma S. Milestone
*Attorney, Agent, or Firm*—Harry A. Pacini

[57] ABSTRACT

The 4-hydroxy-5-isopropyl-2-methylphenyl trimethylammonium 1-piperidine carboxylate salt of N-phosphonomethyl glycine is disclosed herein, having utility as a herbicide.

3 Claims, No Drawings

4-HYDROXY-5-ISOPROPYL-2-METHYLPHENYL TRIMETHYLAMMONIUM, 1-PIPERIDINE CARBOXYLATE SALT OF N-PHOSPHONOMETHYLGLYCINE AND ITS USE AS A HERBICIDE

BACKGROUND OF THE INVENTION

This invention is directed to a novel chemical compound and its use in controlling weeds and regulating the natural growth or development of plants.

It is known that various features of plant growth can be modified or regulated to produce a variety of beneficial effects. For instance, plants can be defoliated and leaf growth inhibited while the productive plant parts remain unaffected. Such action often stimulates extra growth on the productive plant parts and facilitates harvesting operations. Chemical agents producing these effects are particularly useful in flax, cotton, and bean crops, and other crops of a similar nature. While defoliation results in the killing of leaves, it is not a herbicidal action since it does not harm the remainder of the plant. Indeed, killing of the treated plant is undesirable when defoliation is sought, since leaves will continue to adhere to a dead plant.

Another response demonstrated by plant growth regulants is the general retardation of vegetative growth. This response has a wide variety of beneficial features. In certain plants it causes a diminution or elimination of the normal apical dominance, leading to a shorter main stem and increased lateral branching. Smaller, bushier plants with increased resistance to drought and pest infestation are the result. Retardation of vegetative growth is also useful in turf grasses for lessening the vertical growth rate, enhancing root development, and producing a denser, sturdier turf. The retardation of turf grasses also serves to increase the interval between mowings of lawns, golf courses and similar grassy areas.

BRIEF DESCRIPTION OF THE INVENTION

It has now been discovered that the 4-hydroxy-5-isopropyl-2-methylphenyl trimethylammonium, 1-piperidine carboxylate salt of N-phosphonomethylglycine is useful in regulating the natural growth or development of plants and to be phytotoxic to the plants. This salt has the following formula:

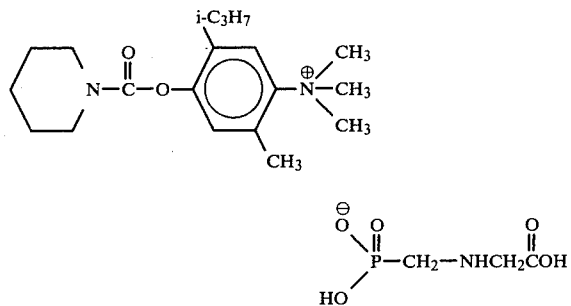

It has also been discovered that the compound of the present invention is useful in controlling undesirable vegetation. Accordingly, the invention further relates to a method of controlling undesirable vegetation, comprising applying to the vegetation in postemergent state a herbicidally effective amount of the compound. Herbicidal effects are generally achieved with a higher application rate than plant growth regulant effects. The compound is particularly effective in controlling grass weeds. The term "herbicidally effective amount" designates any amount which will kill a plant or any portion thereof. The term "plants" is intended to include germinant weeds, emerging seedlings, and established vegetation, including both roots and above-ground portions.

DETAILED DESCRIPTION OF THE INVENTION

Herbicidal effects are achieved by adversely affecting natural growth or development of plants, and the strength of the application can be varied to achieve the desired result. The compound of the instant invention serves to regulate the natural growth or development of treated plants in a number of diverse ways, and it should be understood that the regulatory effects will vary from one plant species to the next or from one application rate to the next.

The compound is readily prepared from N-phosphonomethylglycine by reacting the latter with a 4-hydroxy-5-isopropyl-2-methylphenyltrimethylammonium chloride 1-piperidine carboxylate in the presence of aqueous sodium hydroxide. N-Phosphonomethylglycine is a commercially available material known by the common name "glyphosate." It can be prepared by the phosphonomethylation of glycine, the reaction of ethyl glycinate with formaldehyde and diethylphosphite, or the oxidation of the N-phosphinomethylglycine. Such methods are described in U.S. Pat. No. 3,799,758 (Franz, Mar. 26, 1974). The compound 4-hydroxy-5-isopropyl-2-methylphenyltrimethylammonium chloride 1-piperidine carboxylate is also known as AMO 1618 and can be obtained from Calbiochem®, Compound 1712.

Example 1 illustrates the preparation of the compound and Example 2 illustrates the herbicidal activity. These examples are merely illustrative, non-limiting demonstrations of the preparation of the compound of the present invention and of its effectiveness in controlling undesirable vegetation.

EXAMPLE 1

Preparation of 4-hydroxy-5-isopropyl-2-methylphenyl trimethylammonium 1-piperidine carboxylate Salt of N-Phosphonomethylglycine A sample of mono-isopropylamine salt of N-phosphonomethylglycine was obtained from Monsanto Agricultural Products Co., St. Louis, Mo., in the form of an aqueous solution containing 41% active ingredient by weight. A 51.5 g (0.125 mole) portion of this solution was diluted with 75 ml of water and 10.4 ml of 12 N hydrochloric acid (0.125 mole) was added. The reaction mixture was stirred for an hour, and the solid product was filtered off. The product was washed successively with water, ethanol, and acetone, then dried in an oven. The yield was 15.8 g (75% of theoretical) of N-phosphonomethylglycine.

A 1.2 g (0.01 mole) portion of this material was combined with 3.55 g (0.01 mole) of 4-hydroxy-5-isopropyl-2-methylphenyltrimethylammonium chloride 1-piperidine carboxylate in 50 ml of water with 0.4 g (0.01 mole) sodium hydroxide. The resulting mixture was heated to 80° C. for thirty minutes, cooled and then stripped of water and volatiles. The yield was 11.6 g of 44.8% aqueous solution with 5.2% dissolved sodium chloride. The identity of the product was determined to be the title compound by carbon-13 nuclear magnetic resonance.

EXAMPLE 2

Herbicidal Activity

This example demonstrates the postemergence herbicidal activity of the compound of the present invention in comparison with that of the known isopropylamine salt of N-phosphonomethylglycine.

Aluminum planting flats measuring 15.2×22.9×8.9 cm were filled to a depth of 7.6 cm with loamy sand soil, containing 50 parts per million (ppm) each of the commercial fungicide cis-N[(trichloromethyl)thio]-4-cyclohexene-1,2-dicarboximide (Captan) and 17-17-17 fertilizer (percentages of N-$P_2O_5$-$K_2O$) on a weight basis). Several rows were impressed across the width of each flat and a variety of seeds of both grass and broadleaf weed species were planted, one species per row. The weed species used are listed below:

| Grasses: | |
|---|---|
| A. Foxtail | Setaria sp. |
| B. Watergrass | Echinochloa crusgalli |
| C. Wild oat | Avena fatua |
| D. Yellow nutsedge | Cyperus esculentus |
| Broadleaf weeds: | |
| E. Annual morning glory | Ipomoea purpurea |
| F. Velvet leaf | Abutilon theophrasti |
| G. Mustard | Brassica sp. |
| H. Curly Dock | Rumex crispus |

The broad leaf species were seeded first, and the grasses were seeded four days later. Ample seeds of each species were planted to produce 20 to 50 seedlings per row after emergence, depending on the size of each plant.

Ten days after the grasses were seeded, the emerged seedlings of all species were sprayed with aqueous solutions of the test compounds. The solutions were prepared to such dilutions that a spray rate of 80 gallons per acre (750 liters per hectare) gave from 0.25 to 4.0 pounds of test compound per acre (0.28 to 4.48 kilograms perhectare) as desired for each test. Additional flats not treated at all were used as standards for measuring the extent of weed control in the treated flats.

Nineteen days later, the test flats were compared to the standards and the weeds in each row were rated visually in terms of percent control ranging from 0% to 100%, with 0% representing the same degree of growth as the same row in the standard and 100% representing complete kill of all weeds in the row. All types of plant injury were taken into consideration. The results are shown in Tables I and II, each showing a separate series of tests. The compound presently claimed demonstrates an improvement over the isopropylamine salt in its herbicidal activity on grass weeds at low application rates.

TABLE I

HERBICIDE TEST RESULTS
TEST COMPOUND: 4-hydroxy-5-isopropyl-2-methylphenyl-trimethylammonium 1-piperidine carboxylate salt of N—Phosphonomethylglycine

| Application Rate (lb/A) | Grasses | | | | | Broadleaf Weeds | | | | |
|---|---|---|---|---|---|---|---|---|---|---|
| | A | B | C | D | AVG | E | F | G | H | AVG |
| 4.0 | 100 | 95 | 85 | 0 | 70 | 35 | 45 | 75 | 85 | 60 |

"AVG": average

METHODS OF APPLICATION

Whether it is used as a plant growth regulator or as a herbicide, the compound of the present invention is most useful when applied directly to the plants subsequent to their emergence from the soil. For application at a field site, the compound is generally embodied in a suitable formulation containing additional ingredients and diluent carriers to aid in its dispersal. Examples of such ingredients or carriers are water, organic solvents, dusts, granules, surface active agents, water-in-oil and oil-in-waer emulsions, wetting agents, dispersing agents, and emulsifiers. The formulation generally takes the form of a dust, solution, emulsifiable concentrate, or wettable powder.

A. DUSTS

Dusts are dense powder compositions which combine the active compounds with a dense, free-flowing solid carrier. They are intended for application in dry form and are designed to settle rapidly to avoid being windborne to areas where their presence is not desired.

The carrier may be of mineral or vegetable origin, and is preferably an organic or inorganic powder of high bulk density, low surface area, and low liquid absorptivity. Suitable carriers include micaceous talcs, pyrophyllite, dense kaolin clays, tobacco dust, and ground calcium phosphate rock.

The performance of a dust is sometimes aided by the inclusion of a liquid or solid wetting agent, of ionic, anionic, or nonionic character. Preferred wetting agents include alkylbenzene and alkylnaphthalene sulfonates, sulfated fatty alcohols, amines or acid amides, long chain acid esters of sodium isothionate, esters of sodium sulfosuccinate, sulfated or sulfonated fatty acid esters, petroleum sulfonates, sulfonated vegetable oils, and ditertiary acetylenic glycols. Dispersants are also useful in the same dust compositions. Typical dispersants include methyl cellulose, polyvinyl alcohol, lignin sulfonates, polymeric alkylnaphthalene sulfonates, sodium naphthalene sulfonate, polymethylene bisnaphthalenesulfonate, and sodium-N-methyl-N-(long chain acid) taurates.

In addition, inert absorptive grinding aids are frequently included in dust compositions to aid in the manufacturing of the dust. Suitable grinding aids include attapulgite clay, diatomaceous silica, synthetic fine silica and synthetic calcium and magnesium silicates.

In typical dust compositions, carriers are usually present in concentrations of from about 30 to 90 weight percent of the total composition. The grinding aid usually constitutes about 5 to 50 weight percent, and the wetting agent up to about 1.0 weight percent. Dispersants, when present, constitute up to about 0.5 weight percent, and minor amounts of anticaking and antistatic agents may also be present. The particle size of the entire composition is usually about 30 to 50 microns.

B. SOLUTIONS

Aqueous solutions of the active compounds are prepared such that application at the rate of about 1 to about 200 gallons of solution per acre (about 9 to about 1875 liters per hectare) will provide the required amount of active ingredient. A small amount of non-phytotoxic surfactant typically between 0.05% and 0.5% by weight is usually included to improve the wetting ability of the solution and thus its distribution over the plant surface. Anionic, cationic, nonionic, ampholytic, and zwitterionic surfactants are all useful in this regard.

Suitable anionic surfactants include alkali metal, ammonium, and amine salts of fatty alcohol sulfates having from 8–18 carbon atoms in the fatty chain and sodium salts of alkyl benzene sulfonates having from 9 to 15 carbon atoms in the alkyl chain. Suitable cationic surfactants include dimethyl dialkyl quaternary ammonium halides with alkyl chains of 8 to 18 carbon atoms. Suitable nonionic surfactants include polyoxyethylene adducts of fatty alcohols having 10 to 18 carbon atoms, polyethylene oxide condensates of alkyl phenols with alkyl chains of 6 to 12 carbon atoms and 5 to 25 moles of ethylene oxide condensed onto each mole of alkyl phenol, and polyethylene oxide condensates of sorbitan esters with 10 to 40 moles of ethylene oxide condensed onto each mole of sorbitan ester. Suitable ampholytic surfactants include secondary and tertiary aliphatic amine derivatives with one aliphatic substituent containing 8 to 18 carbon atoms and another containing an anionic water-solubilizing group such as a sulfate or sulfonate. Sodium-3-dodecylaminopropionate and sodium-3-dodecyl amino propane sulfonate are examples. Suitable zwitterionic surfactants include derivatives of aliphatic quaternary ammonium compounds with one aliphatic substituent containing 8 to 18 carbon atoms and another containing an anionic water-solubilizing group. Examples of are 3-(N,N-dimethyl-N-hexadecylammonio)propane-1-sulfonate and 3-(N,N-dimethyl-N-hexadecylammonio)-2-hydroxy propane-1-sulfonate.

C. EMULSIFIABLE CONCENTRATES

Emulsifiable concentrates are solutions in which the active materials and an emulsifying agent are dissolved in a non-watermiscible solvent. Prior to use, the concentrate is diluted with water to form a suspended emulsion of solvent droplets.

Typical solvents for use in emulsifiable concentrates include weed oils, chlorinated hydrocarbons, and non-water-miscible ethers, esters, and ketones.

Typical emulsifying agents are anionic or nonionic surfactants, or mixtures of the two. Examples include long-chain mercaptan polyethoxy alcohols, alkylaryl polyethoxy alcohols, sorbitan fatty acid esters, polyoxyethylene ethers with sorbitan fatty acid esters, polyoxyethylene glycol esters with fatty or rosin acids, fatty alkylol amide condensates, calcium and amine salts of fatty alcohol sulfates, oil-soluble petroleum sulfonates, or preferably mixtures of these emulsifying agents. Such emulsifying agents usually comprise about 1 to 10 weight percent of the total composition.

Typical emulsifiable concentrates contain about 15 to 50 weight percent active material, about 40 to 82 weight percent solvent, and about 1 to 10 weight percent emulsifier. Other additives such as spreading agents and stickers can also be included.

D. WETTABLE POWDERS

Wettable powders are water-dispersible compositions containing the active material, an inert solid extender, and one or more surfactants to provide rapid wetting and prevent flocculation when suspended in water.

Suitable solid extenders include both natural minerals and materials derived synthetically from such minerals. Examples include kaolinites, attapulgite clay, montmorillonite clays, synthetic silicas, synthetic magnesium silicate and calcium sulfate dihydrate.

Suitable surfactants include both nonionic and anionic types, and function as wetting agents and dispersants. Usually one of each is included. Preferred wetting agents are alkylbenzene and alkylnaphthalene sulfonates, sulfated fatty alcohols, amines or acid amides, long chain acid esters of sodium isothionate, esters of sodium sulfosuccinate, sulfated or sulfonated fatty acid esters, petroleum sulfonates, sulfonated vegetable oils, and ditertiary acetylenic glycols. Preferred dispersants are methyl cellulose, polyvinyl alcohol, lignin sulfonates, polymeric alkylnaphthalene sulfonates, sodium naphthalene sulfonate, polymethylene bisnaphthalenesulfonate, and sodium-N-methyl-N(long chain acid) taurates.

Typical wettable powders contain 25 to 90 percent active material, 0.5 to 2.0 percent wetting agent, 0.25 to 5.0 percent dispersant, and from 9.25 to 74.25 weight percent inert extender. Frequently, 0.1 to 1.0 percent of the extender is replaced by a corrosion inhibitor and/or an antifoaming agent.

E. IN GENERAL

In general, any conventional postemergence method of application can be used, including common dusting or spraying equipment. The amount of active ingredient which is effective in producing the desired result, be it herbicidal or growth-regulating, depends on the nature of the plant species to be controlled and the prevailing conditions. Herbicidal effects are usually achieved at 0.1 to 50 pounds active ingredient per acre, preferably 1 to 10, while plant growth regulation is usually achieved at 0.1 to 20 pounds active ingredient per acre, preferably 0.5 to 5. It will be readily apparent to one skilled in the art that compounds of lower activity will require a higher dosage than more active compounds for the same degree of control.

What is claimed is:

1. A compound having the formula

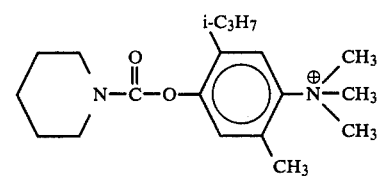

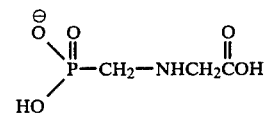

2. A herbicidal composition comprising (a) a herbicidally effective amount of a compound having the formula

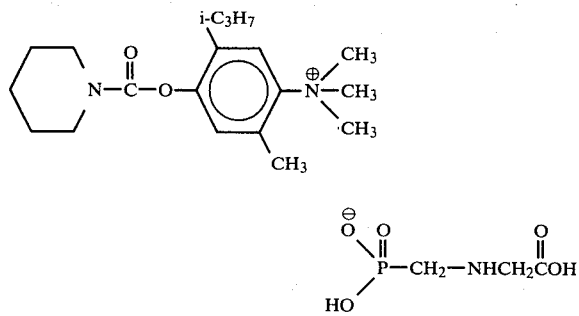
and (b) an inert diluent carrier.
3. A method of controlling undesirable vegetation comprising applying to the vegetation in postemer- gence state (a) a herbicidally effective amount of a compound having the formula
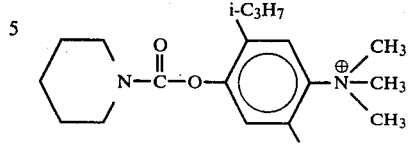
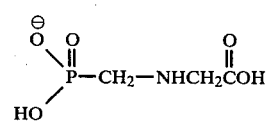
and (b) an inert diluent carrier.
* * * * *